United States Patent [19]

Louis et al.

[11] Patent Number: 4,977,153
[45] Date of Patent: Dec. 11, 1990

[54] 3-AMINOPROPYLOXYPHENYL DERIVATIVES, PHARMACEUTICAL COMPOSITIONS CONTAINING THEM AND METHOD FOR THE THERAPY OF DISEASES

[75] Inventors: William J. Louis, 5 Von Nida Crescent, Rosanna, Victoria, 3084, Australia; Richard Berthold, Bottringen, Switzerland; Max-Peter Seiler, Riehen, Switzerland; Andre Stoll, Birsfelden, Switzerland

[73] Assignee: William J. Louis, Victoria, Australia

[21] Appl. No.: 54,177

[22] Filed: Jan. 14, 1987

Related U.S. Application Data

[63] Continuation of PCT AN86/00135 on May 13, 1986, abandoned.

[30] Foreign Application Priority Data

| May 14, 1985 | [CH] | Switzerland | 2057/85 |
| May 14, 1985 | [CH] | Switzerland | 2061/85 |
| May 14, 1986 | [CH] | Switzerland | 2068/85 |
| May 14, 1986 | [CH] | Switzerland | 2069/85 |
| May 14, 1986 | [CH] | Switzerland | 2070/85 |
| May 14, 1986 | [CH] | Switzerland | 2073/85 |

[51] Int. Cl.$^5$ .................. C09D 33/10; C07C 103/44; C07C 121/75; C07C 127/19; C07C 207/32; C07C 121/80; A61K 31/38; A61K 31/16; A61K 31/17

[52] U.S. Cl. .................. 514/237.5; 514/237.8; 514/259; 514/260; 514/261; 514/383; 514/393; 514/395; 514/398; 514/403; 514/404; 514/405; 514/415; 514/416; 514/418; 514/419; 514/427; 514/438; 514/447; 514/448; 514/459; 514/471; 514/472; 544/134; 544/319; 544/336; 546/153; 546/323; 548/371; 564/47; 564/56; 564/182; 564/186

[58] Field of Search .................. 564/56, 47, 182, 185; 548/371; 544/134, 319, 336; 546/153, 323; 514/237.5, 237.8, 259, 260, 261, 383, 393, 395, 398, 403, 404, 405, 415, 416, 418, 409, 427, 438, 447, 448, 459, 471, 472

[56] References Cited

U.S. PATENT DOCUMENTS

| 3,928,412 | 12/1975 | Smith | 564/182 X |
| 4,010,189 | 3/1977 | Smith | 564/182 X |
| 4,035,420 | 7/1977 | Berntsson et al. | 564/56 X |
| 4,083,992 | 4/1978 | Smith | 564/182 X |
| 4,141,987 | 2/1979 | Smith | 564/182 X |
| 4,327,113 | 4/1982 | Smith | 564/56 X |

FOREIGN PATENT DOCUMENTS 0052072  5/1982  European Pat. Off. .............. 564/56

Primary Examiner—Floyd D. Higel
Attorney, Agent, or Firm—Sughrue, Mion, Zinn, Macpeak & Seas

[57] ABSTRACT

Compounds of formula (I),

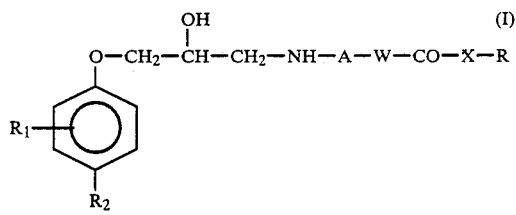

characterized in that R signifies optionally substituted heteroaryl-, heteroarylakyl or heteroarylalkenyl, $R_1$ signifies hydrogen or a substituent, $R_2$ is hydroxy or a group $-z-(CH_2)_n-Y-R_3$ wherein $R_3$ is hydrogen, alkyl, hydroxyalkyl, alkenyl, cycloalkyl, cycloalkylalkylene, hydroxy substituted cycloalkyl or cycloalkylalkylene, or optionally substituted aryl or aralkyl or aralkenyl moiety, and Y signifies oxygen or sulfur, and either Z is an oxygen atom and n is 2 or 3, or Z is a bond and n is 1, 2 or 3, A signifies alkylene or branched alkylene of 2 to 5 carbon atoms, W signifies a bond or imino, and X signifies a bond or imino, and their physiologically hydrolyzable derivatives, in which at least one hydroxy group is in esterified form. The compounds exhibit beta adrenoceptor blocking activity. Processes for the preparation of the compounds are also disclosed.

14 Claims, No Drawings

3-AMINOPROPYLOXYPHENYL DERIVATIVES, PHARMACEUTICAL COMPOSITIONS CONTAINING THEM AND METHOD FOR THE THERAPY OF DISEASES

CROSS REFERENCE TO RELATED APPLICATIONS

This application is a continuation of PCT Application No. AU86/00135, filed May 13, 1986, now abandoned.

The present invention relates to compounds of Formula I,

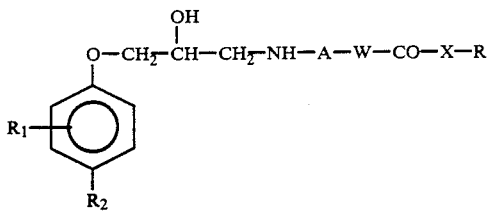

wherein
R signifies optionally substituted heteroaryl-, heteroarylalkyl or heteroarylalkenyl,
$R_1$ signifies hydrogen or a substituent,
$R_2$ is hydroxy or a group $-Z-(CH_2)_n-Y-R_3$
wherein
$R_3$ is hydrogen, alkyl, hydroxyalkyl, alkenyl, cycloalkyl, cycloalkylalkylene, hydroxy substituted cycloalkyl or cycloalkylalkylene, or optionally substituted aryl or aralkyl or aralkenyl moiety, and
Y signifies oxygen or sulfur, and either
Z is an oxygen atom and n is 2 or 3, or
Z is a bond and n is 1, 2 or 3,
A signifies alkylene or branched alkylene of 2 to 5 carbon atoms,
W signifies a bond or imino, and
X signifies a bond or imino,
and their physiologically hydrolysable derivatives, in which at least one hydroxy group is in esterified form.

In accordance with the invention there are especially provided compounds of Formula Ia,

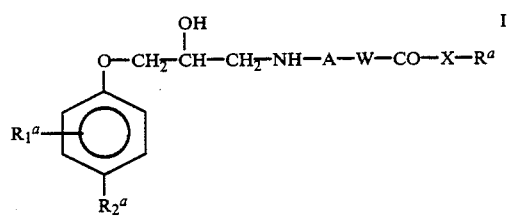

wherein
$R^a$ is furyl, pyranyl, thienyl, pyrrolyl, indolyl, indolinyl, hydroxyindolinyl, purinyl, hydroxypurinyl, oxindolyl, indazolyl, isoindazolyl, benzimidazolyl, benzimidazolonyl, benztriazolyl, quinolinyl, quinolinonyl, isoquinolinyl, isoquinolinonyl, quinazolinyl or quinazolinonyl which is separated from the moiety X by a alkylene chain of 1 to 5 carbon atoms or a alkenylene chain of 2 to 5 carbon atoms and is optionally substituted with alkyl of 1 to 4 carbon atoms, or fused with phenyl or optionally mono- or independently disubstituted phenyl with alkyl of 1 to 4 carbon atoms, alkoxy of 1 to 4 carbon atoms or halogen of atomic number 9 to 53, or any of the above unsaturated ring systems in partly saturated or fully saturated form,
$R_1{}^a$ is hydrogen, hydroxy, alkyl of 1 to 4 carbon atoms, alkoxy of 1 to 4 carbon atoms, alkylthio of 1 to 4 carbon atoms, cycloalkyl of 3 to 7 carbon atoms, halogen of atomic number 9 to 53, trifluoromethyl, pyrol-1-yl, cyano, carbamoyl, alkenyl of 2 to 5 carbon atoms, alkenyloxy of 2 to 5 carbon atoms wherein the double bond is at least one carbon removed from the oxygen, alkanoyl of 2 to 5 carbon atoms, nitro, amino, alkanoylamino of 1 to 5 carbon atoms in the alkoxy position,
$R_2{}^a$ signifies hydroxy or a group $-Z-(CH_2)_n-Y-R_3{}^a$ wherein $R_3{}^a$ is hydrogen, alkyl or hydroxyalkyl of 1 to 5 carbon atoms, alkenyl of 3 to 7 carbon atoms in which the double bond is at least one carbon removed from Y, cycloalkyl or hydroxy substituted cycloalkyl of 3 to 7 carbon atoms, cycloalkylalkyl, hydroxy substituted cycloalkylalkylene of 4 to 8 carbon atoms, phenyl or phenylalkylene of 6 to 10 carbon atoms in which the phenyl moiety can either be unsubstituted or
(i) monosubstituted with hydroxy, halogen, alkyl of 1 to 4 carbon atoms, alkoxy of 1 to 4 carbon atoms or carbamoyl,
(ii) independently disubstituted with hydroxy, alkyl of 1 to 4 carbon atoms, alkoxy of 1 to 4 carbon atoms or carbamoyl,
and A, W, X, Y, n and Z are as defined above, and their physiologically hydrolysable derivatives in which at least one hydroxy group is in esterified form.

A preferred group of compounds of the invention are compounds of Formula Ib,

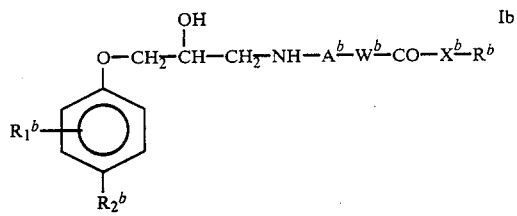

wherein,
$A^b$ is preferably ethylene or trimethylene or branched trialkylene on the -carbon to the nitrogen of the 3-aminopropoxy side chain such as $-CH(CH_3)CH_2-$, $-C(CH_3)_2CH_2-$ or $-C(CH_3)_2(CH_2)_2-$.
$W_b{}^b$ is preferably imino,
$X^b$ is imino or a bond
$R^b$ is a heterocyclic moiety connected to X by either a direct bond or a methylene moiety and is preferably furyl, thienyl, indolyl, isoindazolyl, 2-oxo-1H-indolyl,
$R_1{}^b$ is substituted in the 2 position to the 3-aminopropoxy side chain, by hydrogen, hydroxy, cyano, halogen preferably fluoro, carbamoyl, cycloalkyl or alkyl preferably methyl,
$R_2{}^b$ is hydroxy or a group $Z-(-CH_2)_n-Y-R_3{}^b$ in which $R_3{}^b$ is alkyl or hydroxyalkyl of 1 to 5 carbon atoms, cycloalkylalkyl, hydroxy substituted cycloalkylalkyl of 1 to 6 carbon atoms in the cycloalkyl moiety and 1 to 3 carbon atoms in the alkyl part, optionally substituted phenyl or phenylalkyl with 1 to 3 carbon atoms in the alkyl portion. Substituents on the benzene ring are preferably hydroxy, alkoxy such as methoxy, alkyl such as methyl or halogen such as fluorine, and Y is preferably an oxygen atom,
Z is preferably an oxygen atom,
n is preferably 2,
and physiologically hydrolyzable derivatives thereof having at least one hydroxy group in esterified form.

A preferred group are compounds wherein,
$A^b$, $R_1{}^b$, $R_2{}^b$, and $R^b$ are as defined above and
W is a bond, and
X is imino,
and physiologically hydrolyzable derivatives thereof having at least one hydroxy group in esterified form.

A further preferred group are compounds wherein,
$R_1{}^b$, $A^b$, $R^b$ and $R_2{}^b$ are as defined above and,
W is imino or a bond, and
X is imino or a bond,
and physiologically hydrolyzable derivatives thereof having at least one hydroxy group in esterified form.

Physiologically hydrolysable esters are derivatives, in which under physiological conditions the esterified hydroxy groups are deesterified to give the corresponding hydroxy compound.

An example of an esterified compound is shown as Formula E,

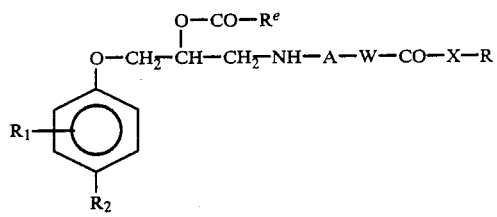

wherein A, W, X, R, $R_1$ and $R_2$ are as defined above and $R_e$ is alkyl of 1 to 12 carbon atoms, cycloalkyl with 3 to 7 carbon atoms, phenyl or phenylalkyl with 7 to 12 carbon atoms.

Preferred are compounds in which the hydroxy group in the 2 position of the 3-aminopropoxy side chain is in unesterified form.

In accordance with the invention the compounds of the invention may be obtained by a process which includes the step of appropriate 3-amino-2-oxypropylating a corresponding compound of Formula II,

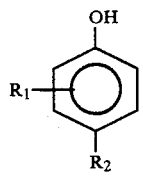

wherein $R_1$ and $R_2$ are as defined above or a precursor form thereof.

The process step of the invention may be effected in conventional manner for the production of analogous 3-amino-2-oxypropoxyaryl compounds. The choice of the most appropriate variants should, of course, take into account the reactivities of the substituents present.

A precursor form of the compound of Formula II is a compound capable of being converted into a compound of Formula II. For example by appropriate etherification, aromatic substitution and/or deprotection; when $R_2$ is a hydroxy substituted phenyl preferably in protected form.

Thus, the process step of the invention may be effected in more than one stage. For example, a compound of Formula II in protected form may be used or a 3-amino-3-oxypropyl moiety in protected form may be introduced and subsequently after 3-amino-2-oxypropylation has been effected the protecting group present may be split off.

Benzyl, methyl or 2-tetrahydropyranyl, but preferably benzyl are examples of a protecting group on for example a hydroxy substituted ring.

In one form of the process according to the invention the 3-amino-2-oxypropylation is effected in two main process stages.

In the first process stage a group $CH_2R_x$ wherein $R_x$ is a group capable of reacting with a primary amine to give a 2-amino-1-hydroxyethyl group is introduced by O-alkylation in the 1 position into a compound of Formula II to give a corresponding compound of Formula III.

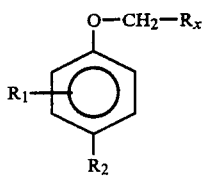

wherein $R_1$, $R_2$ and $R_x$ are as defined above.

In the second process stage compounds of Formula III is aminated with a corresponding compound of Formula IV, $$_2HN-A-W-CO-X-R \qquad IV$$

wherein A, W, X and R as defined above and where required at least one hydroxy group in a resulting compound of Formula I is appropriately esterified.

The alkylation process stage in the 1 position may be effected in the manner known for the production of analogous ethers. A compound of Formula II is preferably reacted in an ionic form. The amination process stage may be effected in conventional manner for the production of analogous 3-amino-2-hydroxypropoxyaryl compound. For example $R_x$ may be a group of Formula

or a derivative of this group for example by a group of Formula $CHOHCH_2L$ wherein L is chlorine, bromine or a group $R_ySO_2O$ wherein $R_y$ is phenyl, tolyl or alkyl. L is especially chlorine. The reaction is preferably effected in ethanol or in an appropriate ether such as dioxane. Optionally an excess of the amine may be used as solvent. Alternatively the reaction may be effected in a fusion melt. Suitable reaction temperature may be from about 20° to about 200°. Conveniently the reflux temperature of the reaction mixture if a solvent is used.

The optional esterification in a resultant compound of Formula I may be affected in a manner known for the production of analogous esters, if necessary using selective conditions when other reactive groups, for example hydroxy or amino are present.

The compounds of the invention may exist in free form, i.e. normally as a base or in salt form. Free forms of the compounds of the invention may be converted into salt forms. For example, acid addition salt forms and vice versa in a conventional manner.

Suitable acids for acid addition salt formation include hydrochloric, malonic, succinic, oxalic and fumaric acids.

In the compounds of the invention the carbon atom in for example the 2 position of the 3-amino-propoxy side chain is asymmetrically substituted and when A is —C$_\alpha$H(CH$_3$)CH$_2$— the alpha carbon atom on the alkylene side chain is also asymmetrically substituted. The compounds may thus exist in racemic form or individual optical isomer forms. The preferred optical isomer has the S-configuration of the asymmetrically substituted carbon atom of the 3-aminopropoxy side chain and when branched on the alkylene side chain the preferred optical isomer has the R-configuration. Individual optical isomer forms may be obtained in conventional manner, for example, by using optically active starting materials or by fractional crystallization of racemate salts using optically active acids.

In so far the preparation of any particular starting materials is not particularly described, this may be effected in conventional manner.

In the following examples all temperatures are in degrees centigrade and are uncorrected.

EXAMPLE 1

N-[2-[3-[2-cyano-4-(2-propoxyethoxy)phenoxy]-2-hydroxypropylamino]-ethyl]-N'-(1H-indol-5-yl)-urea 4.07 g 2-(2,3-Epoxypropoxy)-5-(2-propoxyethoxy)-benzonitrile, 3.2 g N-(2-aminoethyl)-N'-(1H-indol-5-yl)urea and 200 ml methanol are refluxed together for 5 hours. After removal of the solvent by evaporation the frothy residue is purified by silica gel chromatography under reduced (0.5 bar) pressure using ammonia/methanol/dichloromethane (1:9:90) as eluting phase. After recrystallization from ethylacetate/ether the melting point is 122°–124°.

The starting materials are obtained as follows:

(a) 5 g 1H-indol-5-amine is dissolved in 50 ml pyridine and 6.1 g of chloroacetic acid phenyl ester is added dropwise with vigorous stirring to the mixture held at 0°–5°. After 3 hours stirring at room temperature the pyridine is removed by vacuum distillation at 50° and the residue mixed with ice-water and methylenechloride/isopropanol (3:1). After drying of the organic phase with magnesium sulfate and removal of the solvent by evaporation the oily 1H-indol-5-carbamino acid phenyl ester is obtained (used without further purification).

(b) 9.2 g 1H-Indol-5-carbamino acid phenyl ester, 12 ml 1,2-diethylamine and 70 ml dioxane are reacted together with stirring for 2 hours in an oil bath at 100°. After cooling and removal of solvent the residue is mixed with tartaric acid solution and ethylacetate. The aqueous phase is made alkaline with NaOH solution and extracted with dichloromethane/isopropanol (2:1). The extract is dried over magnesium sulfate and evaporated. The crystalline residue is purified over silica gel under reduced (0.5 bar) pressure using conc. ammonia/isopropanol/ethylacetate (5:35:45). Clear fractions are recrystallized from methanol/ether giving N-(2-aminoethyl)-N'-(1H-indol-5-yl) urea (M.P. 156°–158°).

The following examples of Formula I are obtained in like manner to Example 1:

| Example No. | A | W | X | R | $R_1$ | $R_2$ | Y | Z | n | M.P. |
|---|---|---|---|---|---|---|---|---|---|---|
| 2* | —CH₂CH₂— | —NH— | Bond | indol-5-ylmethyl | o-CN | Pr | O | O | 2 | b 118–120° |
| 3** | —CH₂CH₂— | —NH— | Bond | (2-oxoindolin-5-yl)methyl | o-CN | Pr | O | O | 2 | b 93–95° |
| 4 | —CH₂CH₂— | —NH— | —NH— | indol-4-yl | o-CN | Pr | O | O | 2 | b 126–129° |
| 5 | —CH₂CH₂— | —NH— | —NH— | indol-5-yl | o-CN | Pr | O | O | 2 | b 130–132° |
| 6 | —CH₂CH₂— | —NH— | —NH— | indol-6-yl | o-CN | —CH₂ | O | O | 2 | b 115–118° |
| 7 | —CH₂CH₂— | —NH— | —NH— | indol-7-yl | o-CN | Pr | O | O | 2 | b 120–122° |
| 8 | —CH₂CH₂— | —NH— | Bond | indol-4-ylmethyl | o-CN | Pr | O | O | 2 | b 155–159° |

-continued

| Example No. | A | W | X | R | R₁ | R₂ | Y | Z | n | M.P. |
|---|---|---|---|---|---|---|---|---|---|---|
| 9 | —CH₂CH₂— | —NH— | Bond | indol-5-yl-CH₂— | o-CN | Pr | O | O | 2 | b 100-102° |
| 10 | —CH₂CH₂— | —NH— | Bond | thien-2-yl-CH₂— | o-CN | Pr | O | O | 2 | b 87-89° |
| 11 | —CH₂CH₂— | —NH— | Bond | thien-2-yl-CH₂— | o-CN | Pr | O | O | 2 | b 94-96° |
| 12 | —C(Me₂)CH₂— | —NH— | —NH— | indol-5-yl | o-CN | Pr | O | O | 2 | b 57-62° |
| 13 | —CH₂CH₂— | —NH— | —NH— | indol-5-yl | o-CN | Bu | O | O | 2 | b 119-121° |
| 14 | —CH₂CH₂— | —NH— | —NH— | indol-5-yl | o-CN | —CH₂CH₂—C₆H₅ | O | O | 2 | b 114-116° |
| 15 | —CH₂CH₂— | —NH— | —NH— | indol-5-yl | o-CN | —CH₂CH₂—C₆H₄F | O | O | 2 | b 114-116° |

-continued

| Example No. | A | W | X | R | $R_1$ | $R_2$ | Y | Z | n | M.P. |
|---|---|---|---|---|---|---|---|---|---|---|
| 16 | —CH$_2$CH$_2$— | —NH— | —NH— | (4-methylphenyl)-NH-C(CH$_3$)=CH— | o-CN | Pr | O | O | 2 | b 144–145° |
| 17 | —CH$_2$CH$_2$— | —NH— | —NH— | indol-yl | H | Pr | O | O | 2 | b 119–121° |
| 18 | —CH$_2$CH$_2$— | —NH— | —NH— | (methylphenyl)-NH-C(=O)-CH$_2$— | o-CN | Pr | O | O | 2 | b 162–164° |
| 19 | —CH$_2$CH$_2$— | —NH— | —NH— | indol-yl | o-CN | Pr | O | O | 2 | b 116–118° |
| 20 | —CH$_2$CH$_2$— | —NH— | Bond | indol-yl | o-CN | 4-F-C$_6$H$_4$-CH$_2$— | O | O | 2 | b 100–102° |
| 21 | —CH$_2$CH$_2$— | —NH— | Bond | furan-yl | H | cyclopropyl-CH$_2$— | O | O | 2 | b 90–90.5° |
| 22 | —CH$_2$CH$_2$— | —NH— | Bond | furan-yl | o-Br | cyclopropyl-CH$_2$— | O | O | 2 | b 94.5° |
| 23 | —CH$_2$CH$_2$— | —NH— | Bond | furan-yl | H | cyclopropyl-CH$_2$— | O | O | 2 | b 69–70° |

-continued
| Example No. | A | W | X | R | $R_1$ | $R_2$ | Y | Z | n | M.P. |
|---|---|---|---|---|---|---|---|---|---|---|
| 24 | $-CH_2CH_2-$ | $-NH-$ | Bond | 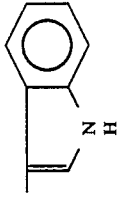 | H | $-CH_2-$ | O | O | 2 | ch 192–194° |
| 25[b] | $-CHCH_2-$ $CH_3$ (R, S) | $-NH-$ | Bond |  | H | Pr | O | O | 2 | hfu 43–50° |
| 26 | $-CH_2CH_2-$ | $-NH-$ | Bond |  | H | Pr | O | O | 2 | b 71–72° |
| 27 | $-CH_2CH_2-$ | $-NH-$ | Bond | 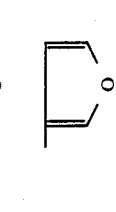 | o-Br | Pr | O | O | 2 | b 77–78° |
| 28 | $-CH_2CH_2-$ | $-NH-$ | Bond |  | H | Pr | O | O | 2 | ch 160–162° |
| 29[c] | $-CH-CH_2-$ $CH_3$ (R) | $-NH-$ | Bond | 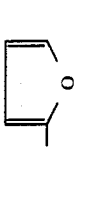 | H | Pr | O | O | 2 | b 63–65° |
| 30[d] | $-CH-CH_2-$ $CH_3$ (R) | $-NH-$ | Bond | 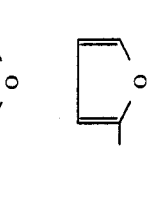 | H | 2-Me—Pr | O | O | 2 | b 64–65° |
| 31[e] | $-CH-CH_2-$ $CH_3$ (R) | $-NH-$ | Bond |  | H | $-CH_2-$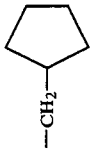 | O | O | 2 | b 83–85° |
| 32 | $-CH_2CH_2-$ | $-NH-$ | Bond |  | H | 2-Me—Pr | O | O | 2 | b 82–84° |

-continued

| Example No. | A | W | X | R | R₁ | R₂ | Y | Z | n | M.P. |
|---|---|---|---|---|---|---|---|---|---|---|
| 33(f) | CH₃<br>▲<br>—CH—CH₂—<br>(R) | —NH— | Bond | 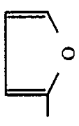 | o-F | Pr | O | O | 2 | b 69–71° |
| 34(g) | CH₃<br>▲<br>—CH—CH₂—<br>(R) | —NH— | Bond |  | o-F | 2-Me—Pr | O | O | 2 | b 72–74° |
| 35 | —CH₂CH₂— | —NH— | Bond |  | H | Pr | O | O | 2 | |
| 36 | —CH₂CH₂— | —NH— | Bond | 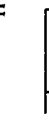 | H | Pr | O | O | 2 | |
| 37 | —CH₂CH₂— | —NH— | Bond | 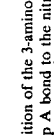 | H | —CH₂—△ | O | O | 2 | |

Me = Methyl  Pr = Propyl  Bu = Butyl  M.P. = Melting Point  b = base  hmo = hydrogen malonate salt  HCl = hydrogen chloride salt  hfu = hydrogen furmarate salt
(a)Ortho to the 3-aminopropoxy side chain
(b)Mixture of 2 diastereomeres with the S-configuration on the carbon atom in the 2-position of the 3-amino propoxy side chain; $[\alpha]_D^{20} = -6.64°$ (c = 1.58/MeOH).
(c)Mixture of 2 diastereomeres with the R configuration on the carbon atom of the group A bond to the nitrogen; $[\alpha]_D^{20} = -8.04°$ (c = 1.9/MeOH).
(d)Mixture of 2 diastereomeres with the R configuration of the carbon atom of the group A; $[\alpha]_D^{20} = 11.43°$ (c = 1.0/MeOH).
(e)Mixture of 2 diastereomeres with the R configuration of the carbon atom of the group A; $[\alpha]_D^{20} = -7.2°$ (c = 1.22/MeOH).
(f)Mixture of 2 diastereomeres with the R configuration of the carbon atom of the group A; $[\alpha]_D^{20} = -7.1°$ (c = 1.57/MeOH).
(g)Mixture of 2 diastereomeres with the R configuration of the carbon atom of the group A; $[\alpha]_D^{20} = -7.30°$ (c = 0.8/MeOH).
*The required intermediate 1H-indol-6-acetic acid ethyl ester is obtained from reaction of ethyliodide with 1-indol-6-acetic acid ethyl ester in tetrahydrofuran in the presence of 1,8-diazabiazalo [5.4.0] undec-7-an (1,5-5).
**The required intermediate 2,3-dihydro-2-oxo-1H-indol-5-acetic acid methyl ester is obtained from reaction of 5-methoxymethyl-1H-indol-2(3H)-one with hydrochloric acid followed by reaction of the obtained chloride with potassium cyanide/water and saponification of 2,3-dihydro-2-oxo-(1H-indol-5-acetonitrile) with potassium hydroxide in ethanol and esterification of the obtained 2,3-dihydro-2-oxo-1H-indol-5-acetic acid with methanol in sulfuric acid.

EXAMPLE 38

4-[3-[2-Cyano-4-(2-propoxyethoxy)phenoxy]-2-hydroxypropylamino]-N-(1H-indol-5-yl)butanamide 3.2 g 2-(2,3-Epoxypropoxy)-5-(2-propoxyethoxy)benzonitrile, 2.5 g of 4-amino-N-(1H-indol-5-yl)butanamide and 160 ml methanol were refluxed together for 4 hours. After removal of the solvent the residue was purified over silica gel under reduced (0.5 bar) pressure using conc. ammonia/methanol/dichloromethane (1:14:85) as eluting solvent. The clear fractions are recrystallised from methanol/ether giving the title compound (M.P.=98°–100°).

The starting materials are obtained as follows:

(a) Three g of 4-aminobutyric acid is dissolved in 2.33 g of sodium hydroxide and 30 ml water. After addition of 30 ml chloroform the mixture is cooled to 10° and 5.46 g chloroacetic acid benzyl ester is added dropwise with vigorous stirring. After leaving to stand with stirring at room temperature overnight dichloromethane is added and the mixture allowed to partition. The aqueous phase is saturated with sodium chloride and extracted with methylene chloride. After drying over magnesium sulfate the solvent is removed by evaporation in vacuo giving the oily 4-(benzyloxycarbamoylamino)butyric acid.

(b) 6.76 g of 4-(Benzyloxy-carbonylamino)butyric acid is dissolved in 70 ml dichloromethane and reacted with 2.94 g dicyclohexylcarbodiimide at room temperature. After 2 hours stirring the precipitate is filtered, washed with 25 ml dichloromethane and reacted with 3.6 g sodium hydrogen carbonate and 3.44 g 5-aminoindole. After 17 hours stirring at room temperature 150 ml water is added and after a half hour vigorous stirring the dichloromethane phase is removed and the aqueous phase reextracted twice more with dichloromethane which is finally dried over magnesium sulfate. After removal of the solvent the oily residue is purified over silica gel under reduced pressure (0.5 bar) using toluene-/ethylacetate (2:1) giving 4-(benzyloxycarbonylamino)-N-(1H-indol-5-yl)butanamide (oil).

(c) 4.56 of 4-(Benzyloxycarbonylamino)-N-(1H-indol-5-yl)butanamide, 1.1 g palladium (10%) on charcoal and 100 ml methanol are added together at room temperature in the presence of hydrogen until about 90% of theoretical hydrogen uptake is obtained (maximum uptake). The suspension is filtered through talc and the solvent evaporated off giving an oily residue of 4-amino-N-(1H-indol-5-yl)butanamide which is recrystallised from methanol/ether (M.P. 124°–136°).

The following example is obtained in analogous manner to Example 35.

In particular the compounds possess beta adrenoceptor blocking activity as indicated by standard tests for example, in the spontaneously beating guinea pig atrium (A. Bertolet et al., Postgraduate Medical Journal, 57, Suppl. 1, 9–17, 1981). They inhibit the positive chronotropic isoproterenol effect at bath concentrations from about $10^{-9}$ to $10^{-8}$ mol/l.

Thus, in the test above selected compounds have the following potencies expressed as a dose which doubles the concentration of isoproterenol needed to elicit a 50% increase in heart rate (i.e. ID$_{50}$).

| Example No. | Guinea Pig Atrium, Effective Molar Dose, M (ID50) |
|---|---|
| 1 | $3.0 \times 10^{-9}$ |
| 4 | $2.2 \times 10^{-9}$ |
| 5 | $1.2 \times 10^{-9}$ |
| 6 | $1.3 \times 10^{-8}$ |
| 9 | $2.5 \times 10^{-8}$ |
| 11 | $1.2 \times 10^{-8}$ |
| 14 | $1 \times 10^{-8}$ |
| 19 | $1 \times 10^{-7}$ |
| 20 | $5 \times 10^{-8}$ |
| 29 | $3 \times 10^{-8}$ |
| 33 | $8 \times 10^{-9}$ |
| Propranolol | $3 \times 10^{-9}$ |
| Atenolol | $2 \times 10^{-7}$ |
| Metoprolol | $1.2 \times 10^{-8}$ |

The beta adrenoceptor blocking activity in the heart can also be demonstrated in a whole animal model. For example the inhibition of isoproterenol-induced tachycardia in the pithed rat show in vivo potencies many times higher than expected from their potencies in the guinea pig atrium model and for standard compounds known in the art.

Thus, in the test above, the following compounds exhibit effective beta adrenoceptor blocking activity at doses indicated below:

| Example No. | Pithed Rat Effective Dose (ID50) (ug/kg) |
|---|---|
| 1 | 2 |
| 5 | 2 |
| 19 | 100 |
| 23 | 30 |
| 27 | 5 |
| 28 | 3 |
| 29 | 50 |
| Propranolol | 20 |
| Atenolol | 30 |
| Betaxolol | 10 |

| Example | A | W | X | R | R1* | R2 | Z | Y | n | M.P. |
|---|---|---|---|---|---|---|---|---|---|---|
| 39 | —(CH₂)₂— | Bond | —NH | 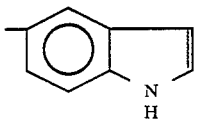 | O—CN | Pr | O | O | 2 | 117–119° | b = base
*o = ortho to 3-aminopropoxy side chain

The compounds of the invention in free form or as their physiologically acceptable salt possess unique pharmacological activity and can be used as therapeutic agents in man.

The compounds are particularly useful as beta adrenoceptor blocking agents and can therefore be used for the prophylaxis and therapy of diseases which are commonly known to respond to blockade of beta adrenoceptors such as those found in the heart. Examples of such diseases are hypertension, angina pectoris, thyrotoxicosis, migraine, glaucoma and for the treatment of disturbances of the heart rhythm such as supraventricular tachycardia.

In addition, the compounds have more marked and wider spread beneficial pharmacological properties than would be expected for compounds having this type of structure. In particular, their activity is more cardioselective than presently known for similar compounds. This can be demonstrated in vivo in tracheal preparations of the guinea pig which are prepared according to standard procedures in which a portion of the tracheal muscle is allowed to relax under the influence of isoproterenol and in the presence of known concentrations of the compound to be tested. Selected examples are shown below:

| Example No. | Guinea Pig Trachea Effective Molar Dose, ID50 |
|---|---|
| 1 | $5 \times 10^{-5}$ |
| 4 | $>1 \times 10^{-4}$ |
| 5 | $4 \times 10^{-5}$ |
| 6 | $5 \times 10^{-5}$ |
| 9 | $2 \times 10^{-5}$ |
| 11 | $4 \times 10^{-6}$ |
| 14 | $5 \times 10^{-5}$ |
| 19 | $5 \times 10^{-5}$ |
| 20 | $6 \times 10^{-5}$ |
| 29 | $6 \times 10^{-5}$ |
| 33 | $6 \times 10^{-5}$ |
| Betaxolol | $1 \times 10^{-6}$ |
| Atenolol | $3 \times 10^{-6}$ |
| Propranolol | $5 \times 10^{-9}$ |

In these preparations the potency of all examples are much less than in the atrial preparations described above and most have no blocking activity in the tracheal preparation at concentrations of $1 \times 10^{-5}$ molar and for many compounds much higher concentrations than $1 \times 10^{-5}$ molar are needed to show blocking activity in the trachea indicating that these compounds have virtually absolute selectivity for the cardiac (atrial) beta adrenoceptors. In contrast, the cardioselective antagonists betaxolol and atenolol have significant blocking actions of the isoproterenol response in the trachea. Selectivity indices for the compounds disclosed are for the most part impossible to calculate due to their cardiospecificity. For the more potent compounds, e.g. examples 1 and 4, the selectivities are 17000 and 45000 respectively whereas the selectivities for betaxolol and atenolol are 29 and 20 respectively. This indicates that the disclosed examples are to all intents and purposes highly potent cardiospecific β-adrenoceptor antagonists.

In pithed rat preparations many of the compounds can produce a 100% inhibition of the effects of isoproterenol administered in the dose of 0.1 ug/kg i.v. on heart rate but do not inhibit the fall in blood pressure produced by isoproterenol at doses as high as 300 ug/kg i.v. This fall in blood pressure largely reflects a beta 2 effect of isoproterenol on peripheral blood vessels and is further proof of the high beta 1 selectivity of the compounds in vivo.

The high selectivity of blockade for these compounds is of major importance in the treatment of hypertension where exacerbation of an existing asthmatic condition may be precipitated by currently commercially available compounds. Highly selective compounds would be expected to have fewer adverse metabolic effects such as elevation of blood cholesterol and fewer vasospasm effects such as Raynaud's symptoms.

Some of the compounds also possess a degree of intrinsic sympathomimetic activity (ISA), a property which is useful in preventing undue bradycardia and helps reduce the incidence of heart failure in subjects with heart muscle disease. This property is also believed to be useful in reducing the incidence of rebound hypersensitivity occurring after cessation of beta blocking drugs which has been described with such drugs with no ISA like propranolol as well as reducing the incidence of adverse metabolic effects such as the elevated plasma cholesterol produced by drugs like propranolol which lack ISA.

This property can be demonstrated as an increase in resting heart rate in a pithed rat preparation using standard procedures in which the maximum effect of cumulative doses of drug up to 3 mg/kg are observed. Selected examples which show this activity are shown below:

| Example No. | Maximum Change in Resting Heart Rate in the Pithed Rat |
|---|---|
| 1 | +101 |
| 5 | +119 |
| 11 | +66 |
| 13 | +105 |
| 19 | +51 |
| 23 | +42 |
| Propranolol | 0 |
| Atenolol | 0 |
| Betaxolol | 0 |
| Pindolol | +89 |

In some of these compounds the degree of beta agonist activity is such that when added to the selective beta antagonist properties the compounds are useful as cardiotonics e.g. for the treatment of heart insufficiency, especially in situations where a positive inotropic effect is desired without significant influence on blood pressure. The balance between the agonistic and antagonistic activities is particularly favourable for these compounds: the agonistic component contributes to the cardiotonic activity while the antagonistic component protects against an excessive increase in contractile force which might lead to arrhythmias. Compounds in which $R_2$ is hydroxy show an added degree of partial agonist activity which is most useful in the treatment of cardiac insufficiency particularly in situations where a prolonged drug effect is not wanted.

These compounds also show the added advantage of lowering intraocular pressure when instilled as a buffered solution to the cornea of the eyes. Thus, those compounds can therefore be used for the treatment of glaucoma. This property can be demonstrated using a standard test in rabbits. Reductions in intraocular pressure are observed by as much as 4 mm Hg over a 2 hr period.

For these uses described above, the dose will vary according to the substance used, the mode of administration and the desired treatment. In general, however, the dose required to treat hypertension and related coronary heart diseases with an oral formulation of compounds 1 to 36 are obtained with a daily dosage of 0.5 to 5 mg per kg body weight: administration may be affected in 1, 2 or 3 divided doses or in a sustained release form. For larger mammals such as man the total daily dosage of these compounds is from about 1 to 600

We claim:
1. A compound of the formula I,

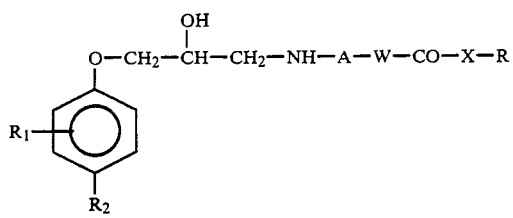

wherein
R represents furyl, pyranyl, thienyl, pyrrolyl, indolyl, indolinyl, hydroxyindolinyl, purinyl, hydroxypurinyl, oxindolyl, indazolyl, isoindazolyl, benzimidazolyl, benzimidazolonyl, benztriazolyl, quinolinyl, quinolinonyl, isoquinolinyl, isoquinolinonyl, quinazolinyl or quinazolinonyl which is separated from the moiety X by an alkylene chain of 1 to 5 carbon atoms or an alkenylene chain of 2 to 5 carbon atoms and is unsubstituted or substituted with alkyl of 1 to 4 carbon atoms, or fused with phenyl or phenyl mono- or independently disubstituted with alkyl of 1 to 4 carbon atoms, alkoxy of 1 to 4 carbon atoms or halogen of atomic number 9 to 53, or any of the above unsaturated ring systems in partly saturated or fully saturated form, $R_1$ represents hydrogen, hydroxy, alkyl of 1 to 4 carbon atoms, alkoxy of 1 to 4 carbon atoms, alkylthio of 1 to 4 carbon atoms, cycloalkyl of 3 to 7 carbon atoms, halogen of atomic number 9 to 53, trifluoromethyl, pyrol-1-yl, cyano, carbamoyl, alkenyl of 2 to 5 carbon atoms, alkenyloxy of 2 to 5 carbon atoms wherein the double bond is at least one carbon removed from the oxygen, alkanoyl of 2 to 5 carbon atoms, nitro, amino, alkanoylamino of 1 to 5 carbon atoms in the alkoxy moiety, $R_2$ represents a physiologically hydrolyzable ester group or a group $—Z—(CH_2)_n—Y—R_3$ wherein $R_3$ is hydrogen, alkyl or hydroxyalkyl of 1 to 5 carbon atoms, alkenyl of 3 to 7 carbon atoms in which the double bond is at least one carbon removed from Y, cycloalkyl or hydroxy substituted cycloalkyl of 3 to 7 carbon atoms, cycloalkylalkyl or hydroxy substituted cycloalkylalkyl of 4 to 8 carbon atoms, phenyl or phenylalkyl of 6 to 10 carbon atoms in which the phenyl moiety is unsubstituted or
(i) monosubstituted with hydroxy, halogen, alkyl of 1 to 4 carbon atoms, alkoxy of 1 to 4 carbon atoms or carbamoyl, or
(ii) independently disubstituted with hydroxy, alkyl of 1 to 4 carbon atoms, alkoxy of 1 to 4 carbon atoms or carbamoyl, A represents alkylene or branched alkylene of 2 to 5 carbon atoms,
W represents a bond or imino,
X represents a bond or imino, and
Y represents oxygen or sulfur, and Z is oxygen and n represents 2 or 3, or
Z is a bond and n represents 1, 2 or 3
or a physiologically hydrolyzable derivative having at least one esterified hydroxy group.

2. A compound as claimed in claim 1 wherein
A is ethylene or trimethylene or branched trialkylene on the α-carbon to the nitrogen of the 3-aminopropoxy side chain,
W is imino,
X is imino or a bond,
R is heterocyclic connected to X by either a direct bond or methylene,
$R_1$ is substituted in the 2 position to the 3-aminopropoxy side chain, by hydrogen, hydroxy, cyano, halogen, carbamoyl, cycloalkyl or alkyl,
$R_2$ is a group $Z—(—CH_2)_n—Y—R_3$ in which $R_3$ is alkyl of 1 to 5 carbon atoms, cycloalkylalkyl of 1 to 6 carbon atoms in the cycloalkyl moiety and 1 to 3 carbon atoms in the alkyl moiety, unsubstituted or substituted phenyl or phenylalkyl with 1 to 3 carbon atoms in the alkyl moiety,
Y is oxygen,
Z is oxygen, and
n is 2,
or a physiologically hydrolyzable derivative thereof having at least one esterified hydroxy group.

3. A compound as claimed in claim 2, wherein R is a furyl, thienyl, indolyl, isoindazolyl, or 2-oxo-1H-indolyl.

4. A compound as claimed in claim 2, wherein $R_1$ is fluoro, cyano or methyl.

5. A compound as claimed in claim 2, wherein
$R_2$ is a group $Z—(CH_2)_n—Y—R_3$ in which $R_3$ is substituted cycloalkyl, substituted cycloalkylalkyl, or substituted phenyl or phenylalkyl with 1 to 3 carbon atoms in the alkyl moiety, wherein the substituents on the rings are hydroxy, methoxy, fluorine or methyl, and
Y is oxygen,
Z is oxygen, and
n is 2.

6. A compound as claimed in claim 1 wherein
A is ethylene or trimethylene or branched trialkylene on the α-carbon to the nitrogen of the 3-aminopropoxy side chain,
W is imino,
R is heterocyclic connected to X by either a direct bond or methylene,
$R_1$ is substituted in the 2 position to the 3-aminopropoxy side chain, by hydrogen, hydroxy, cyano, halogen, carbamoyl, cycloalkyl or alkyl, and
$R_2$ is a physiologically hydrolyzable ester group,
or a physiologically hydrolyzable derivative thereof having at least one additional esterified hydroxy group.

7. A compound as claimed in claim 6, wherein R is furyl, thienyl, indolyl, isoindazolyl or 2-oxo-1H-indolyl.

8. A compound as claimed in claim 1 wherein
A is ethylene or trimethylene or branched trialkylene on the α-carbon to the nitrogen of the 3-aminopropoxy side chain,
R is heterocyclic connected to X by either a direct bond or methylene,
$R_1$ is substituted in the 2 position to the 3-aminopropoxy side chain, by hydrogen, hydroxy, cyano, halogen, carbamoyl, cycloalkyl or alkyl,
$R_2$ is a group $Z—(—CH_2)_n—Y—R_3$ in which $R_3$ is alkyl of 1 to 5 carbon atoms, cycloalkylalkyl of 1 to 6 carbon atoms in the cycloalkyl moiety and 1 to 3 carbon atoms in the alkyl moiety, unsubstituted or substituted phenyl or phenylalkyl with 1 to 3 carbon atoms in the alkyl moiety, and wherein W is a bond, and X is imino, or a physiologically hydrolyzable derivative thereof having at least one esterified hydroxy group.

9. A compound as claimed in claim 1, wherein

A is ethylene or trimethylene or branched trialkylene on the α-carbon to the nitrogen of the 3-aminopropoxy side chain, R is furyl, thienyl, indolyl, isoindazolyl, or 2-oxo-1H-indolyl, $R_1$ is fluoro, cyano or methyl, $R_2$ is a group $Z—(CH_2)_n—Y—R_3$ in which $R_3$ is substituted cycloalkyl, substituted cycloalkylalkyl, or substituted phenyl, or phenylalkyl with 1 to 3 carbon atoms in the alkyl moiety, wherein the substituents on the rings are hydroxy, methoxy, fluorine or methyl, and where X and W are imino or a bond, or a physiologically hydrolyzable derivative thereof having at least one esterified hydroxy group.

10. A compound as claimed in claim 1, wherein

A is ethylene or trimethylene or branched trialkylene on the α-carbon to the nitrogen of the 3-aminopropoxy side chain, R is furyl, thienyl, indolyl, isoindazolyl, or 2-oxo-1H-indolyl, $R_1$ is fluoro, cyano or methyl, $R_2$ is a group $Z—(CH_2)_n—Y—R_3$ in which $R_3$ is substituted cycloalkyl, substituted cycloalkylalkyl, or substituted phenyl or phenylalkyl with 1 to 3 carbon atoms in the alkyl moiety, wherein the substituents on the rings are hydroxy, methoxy, fluorine or methyl, and where W and X are imino or a bond and $R_2$ is hydroxy.

11. A compound as claimed in claim 1, wherein

A is ethylene or trimethylene or branched trialkylene on the α-carbon to the nitrogen of the 3-aminopropoxy side chain, R is furyl, thienyl, indolyl, isoindazolyl, or 2-oxo-1H-indolyl, $R_1$ is fluoro, cyano or methyl, $R_2$ is a group $Z—(CH_2)_n—Y—R_3$ in which $R_3$ is substituted cycloalkyl, substituted cycloalkylalkyl, or substituted phenyl or phenylalkyl with 1 to 3 carbon atoms in the alkyl moiety, wherein the substituents on the rings are hydroxy, methoxy, fluorine or methyl, and where W is a bond, X is imino and where $R_2$ is hydroxy.

12. A compound as claimed in any one of claims 1 or 2-11 which is in the optically active (S)- form at the carbon atom in the 2-position of the 3-aminopropoxy side chain.

13. A pharmaceutical composition comprising (i) a compound of any one of claims 1 or 2-11 in free form or in a pharmaceutically acceptable salt form, and (ii) a pharmaceutical carrier or diluent.

14. A method for the prophylaxis or therapy of diseases responding to blockade of beta adrenoceptors including hypertension or myocardial infarction or sympathetic overstimulation or migraine or glaucoma or thyrotoxicosis or heart rhythm disorders or cardiac failure comprising administering a therapeutically effective amount of a compound or composition as claimed in any one of claims 1 or 2 to 11 to a patient in need of the same.

* * * * *